(12) United States Patent
Levesque et al.

(10) Patent No.: US 9,746,402 B2
(45) Date of Patent: Aug. 29, 2017

(54) MOLDING GRIP FIXTURE

(71) Applicant: ILLINOIS TOOL WORKS INC., Glenview, IL (US)

(72) Inventors: Philippe Levesque, Foxborough, MA (US); Daniel Minahan, Weymouth, MA (US); Miles Malone, West Palm Beach, FL (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 290 days.

(21) Appl. No.: 14/795,258

(22) Filed: Jul. 9, 2015

(65) Prior Publication Data

US 2016/0069783 A1 Mar. 10, 2016

Related U.S. Application Data

(60) Provisional application No. 62/047,091, filed on Sep. 8, 2014.

(51) Int. Cl.
*G01N 1/36* (2006.01)
*G01N 3/04* (2006.01)

(52) U.S. Cl.
CPC ....... *G01N 3/04* (2013.01); *G01N 2203/0089* (2013.01); *G01N 2203/0298* (2013.01); *G01N 2203/0452* (2013.01)

(58) Field of Classification Search
CPC ....... G01N 1/36; G01N 2001/366; G01N 3/04
See application file for complete search history.

(56) References Cited

U.S. PATENT DOCUMENTS

| 4,537,080 A * | 8/1985 | Christiansen ............ G01N 3/04 73/854 |
| 5,945,607 A * | 8/1999 | Peppel ...................... G01N 3/04 73/831 |
| 2013/0199304 A1* | 8/2013 | Hanswillemenke ..... G01N 3/02 73/818 |

\* cited by examiner

*Primary Examiner* — James Sanders
(74) *Attorney, Agent, or Firm* — McCarter & English, LLP

(57) ABSTRACT

The present grip design includes a two-piece clamp with an interior space which forms a mold for the sample material. The two-piece clamp further includes undercut apertures which engage complementary tapered portions of upper and lower grips. The sample material can be poured to fill the mold formed within the two-piece clamp. The interior of the upper and lower grips includes a pattern, such as, but not limited to, a threaded pattern, in order to more firmly engage the sample. The samples may include soft materials, liquids, gels, compounds, powdered or similar materials. The grip may be used in connection with bioreactor or materials testing applications.

18 Claims, 10 Drawing Sheets

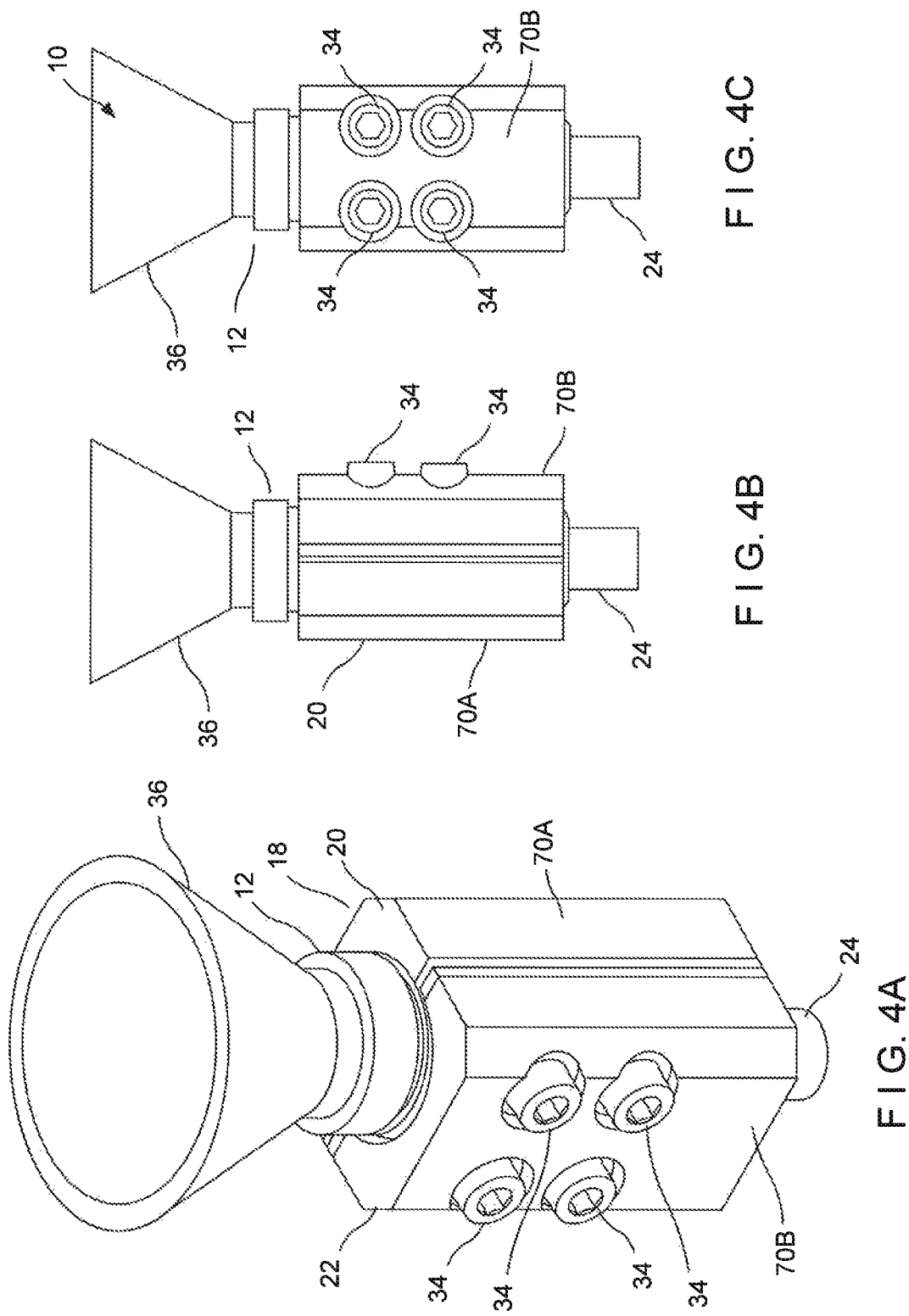

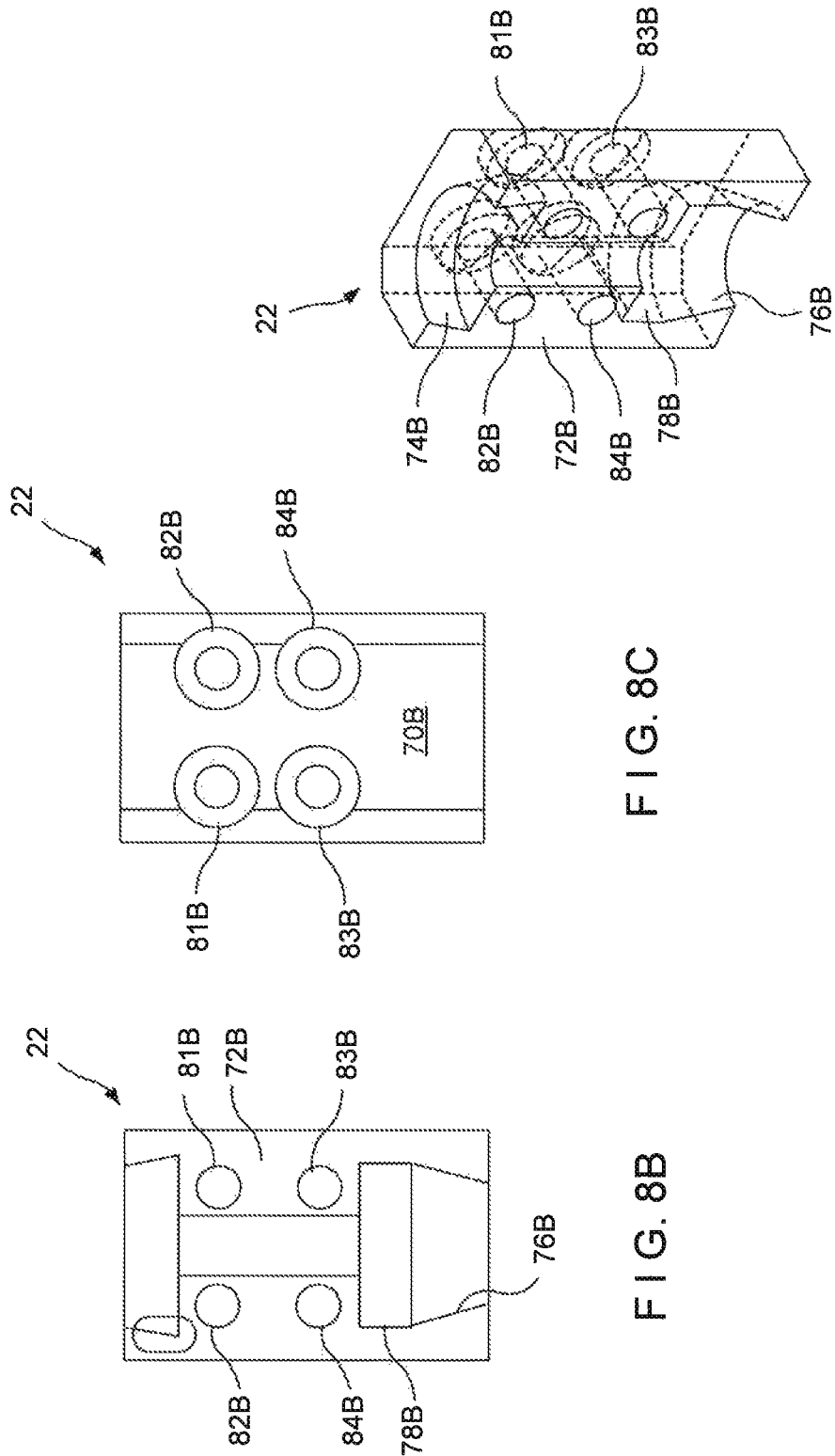

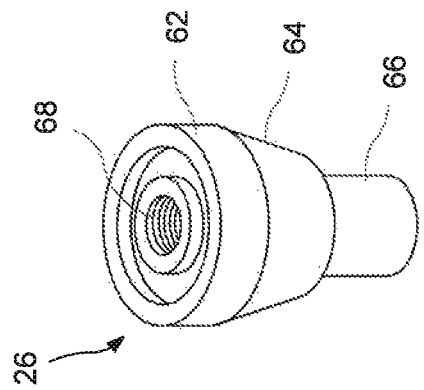
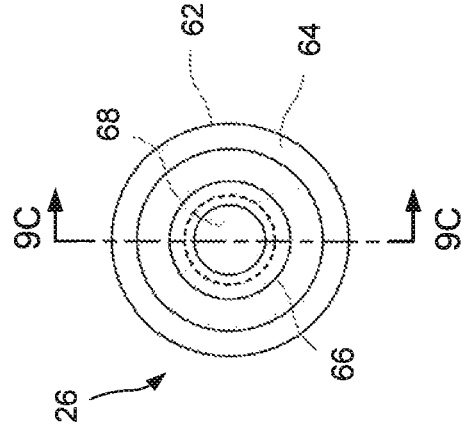
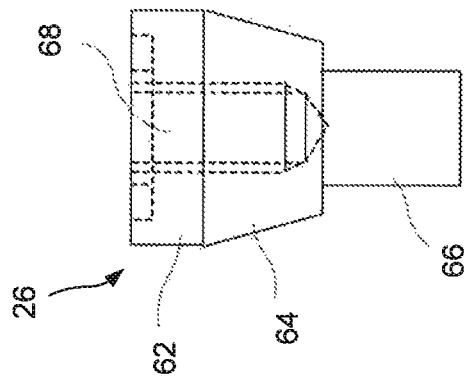

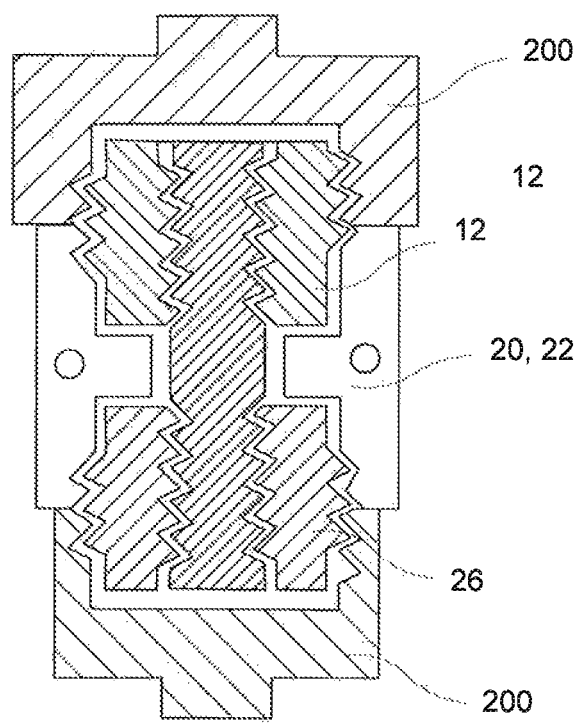
F I G. 10

MOLDING GRIP FIXTURE

This application claims priority under 35 U.S.C. 119(e) of U.S. provisional application Ser. No. 62/047,091, filed on Sep. 8, 2014, the contents of which is hereby incorporated by reference in its entirety and for all purposes.

BACKGROUND OF THE DISCLOSURE

Field of the Disclosure

The present disclosure pertains to a test sample preparation fixture, such as, but not limited to, a grip or grip holder which can be used with soft materials, liquids, gels, compounds, powdered or similar materials. This may be used in connection with bioreactor or materials testing applications, or similar tests involving pouring material into a mold.

Description of the Prior Art

In the field of bioreactors, typical prior art grips from the materials testing field are too big for the sample sizes that are involved.

Moreover, these prior art grips would frequently crush the samples in the bioreactor field as the materials or samples are difficult to clamp between standard grip faces due to their lack of stiffness. The materials or samples may be crushed under very small compressive forces during tensile tests which can lead to test failure or inconsistent test results.

Some bioreactor grips can accommodate small sample sizes in the 1 to 4 millimeter thickness and 1 to 5 millimeter width range. However, these compression grips present flat faces and would crush or tear through gel material samples.

In order to measure very small loads, the grips used to clamp the samples typically must be very light. This allows for the use of small capacity load cells that offer better resolution to detect small load variations generated during the tensile test. If the resolution is too poor, the sample-generated load can get lost in the noise of the load cell or be barely perceptible.

The object of this disclosure is to provide a gripping solution for very low force tensile tests and very soft and compliant materials, such as may be encountered in bioreactor applications. Various elements of the disclosure, such as the material used in their fabrication and their internal surfaces or textures could be changed to modulate the gripping force, weight and applicable test sample materials, without departing from the intent of the disclosure.

SUMMARY OF THE DISCLOSURE

The present grip design includes a two-piece clamp with an interior space which forms a portion of a mold for the sample material. The two-piece clamp further includes undercut apertures which engage complementary tapered portions of upper and lower grips. The sample material can be poured through a funnel to fill the mold formed within the two-piece clamp. The interior of the upper and lower grips includes a pattern, such as, but not limited to, a threaded pattern, in order to increase the surface area and to more firmly engage the sample. The samples may include soft materials, liquids, gels, compounds, powders or similar materials. The grip may be used in connection with bioreactor or material testing applications.

BRIEF DESCRIPTION OF THE DRAWINGS

Further objects and advantages of the disclosure will become apparent from the following description and from the accompanying drawings, wherein:

FIG. 4A is a perspective view of an embodiment of the grip of the present disclosure, including funnel in place of the top grip.

FIG. 4B is a front view of an embodiment of the grip of the present disclosure, including funnel in place of the top grip.

FIG. 4C is a side view of an embodiment of the grip of the present disclosure, including funnel in place of the top grip.

FIG. 8A is a perspective view, partially in phantom, of the counterbore side of the body of the present disclosure.

FIG. 8B is an interior plan view of the counterbore side of the body of the present disclosure.

FIG. 8C is an exterior plan view of the counterbore side of the body of the present disclosure.

FIG. 9A is a perspective view of the bottom grip of the present disclosure.

FIG. 9B is a top plan view, partially in phantom, of the bottom grip of the present disclosure.

FIG. 9C is a cross-sectional view along plane 9C-9C of FIG. 9B.

FIG. 10 is a cut-away view of the assembled grip, including a sample, of the present disclosure.

DETAILED DESCRIPTION OF THE PREFERRED EMBODIMENT

Figure 1:
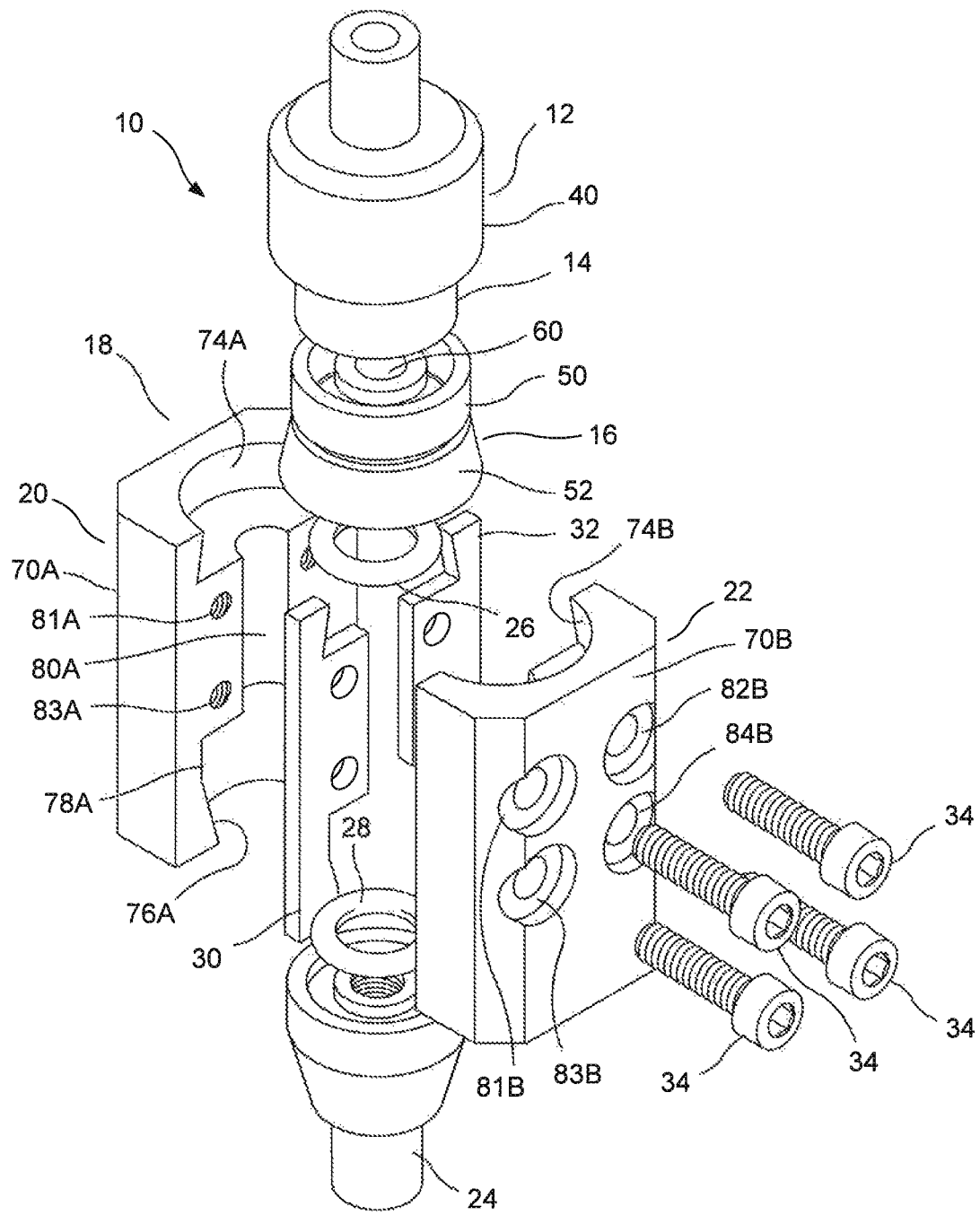
FIG. 1 is an exploded view of an embodiment of the grip of the present disclosure.
Figure 2:
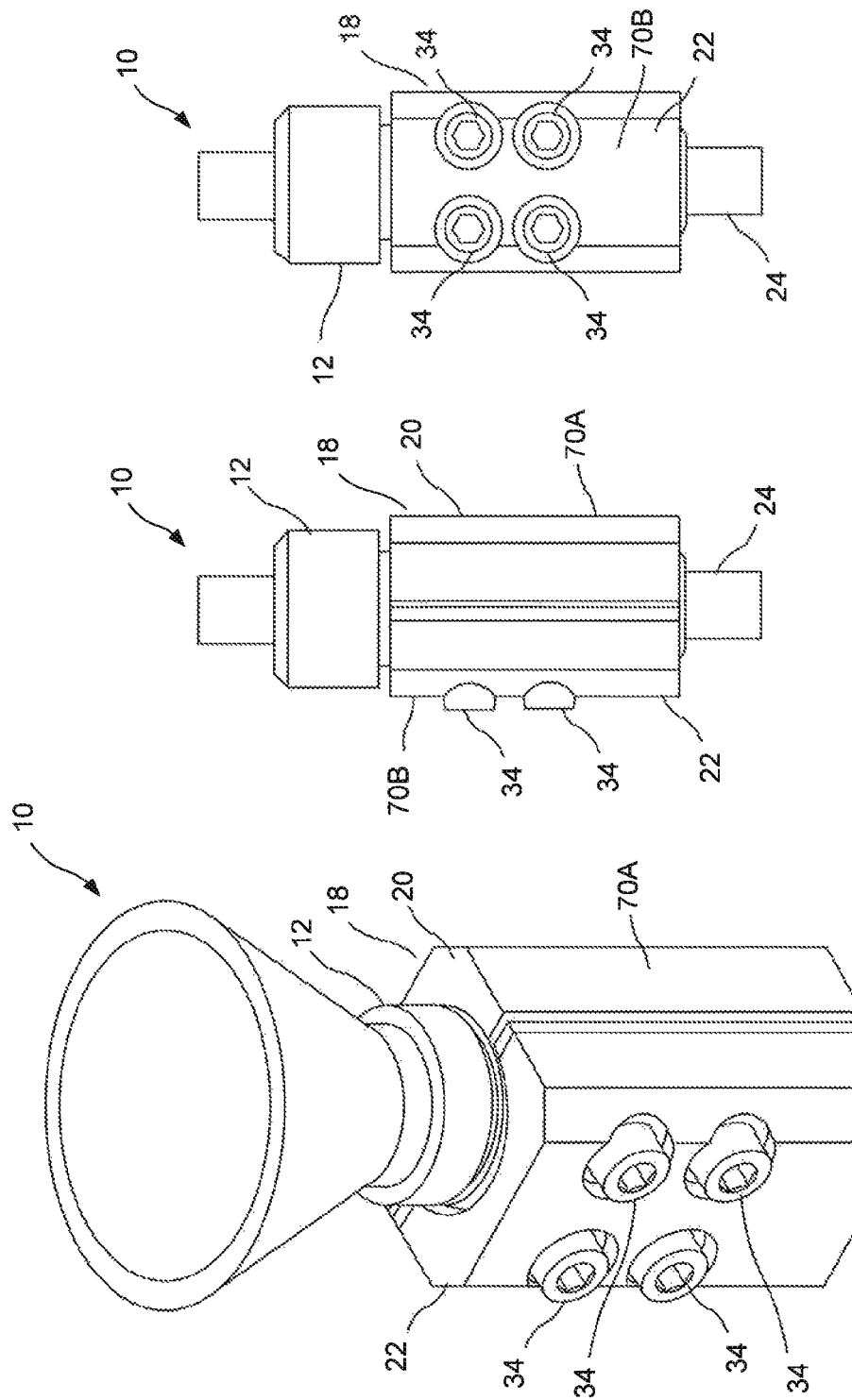
FIG. 2A is a perspective view of an embodiment of the grip of the present disclosure.
FIG. 2B is a front view of an embodiment of the grip of the present disclosure.
FIG. 2C is a side view of an embodiment of the grip of the present disclosure.

Referring to the drawings in detail wherein like numerals indicate like elements throughout the several views, one sees that FIG. 1 illustrates an exploded view of an embodiment of the grip 10 of the present disclosure. Starting generally from the top of FIG. 1, one sees that grip 10 includes a top grip 12 (also known as a grip insert holder, illustrated in further detail in FIGS. 5A, 5B and 5C) which engages a cylindrical rubber seal 14 which serves as a spacer to grip insert 16 (illustrated in further detail in FIGS. 6A, 6B, 6C and 6D). Grip insert 16 is engaged between a two-piece clamp 18 formed from threaded side 20 (illustrated in further detail in FIGS. 7A and 7B) and counterbore side 22 (illustrated in more detail in FIGS. 8A, 8B and 8C). The two-piece clamp 18 similarly engages bottom grip 24 (illustrated in more detail in FIGS. 9A, 9B and 9C). Two-piece clamp 18 further engages first and second O-rings 26, 28 and grip base rubber seals 30, 32. Sides 20, 22 of two-piece clamp 18 are held in place by screws 34 to achieve the configuration illustrated in FIGS. 2A, 2B and 2C.

FIGS. 3, 4A, 4B and 4C illustrate a configuration wherein the grip insert holder or top grip 12 is replaced by a funnel 36.

Figure 5A:
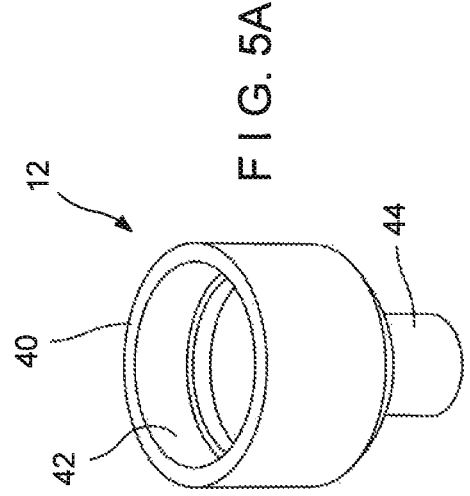
FIG. 5A is a perspective view of the top grip (grip insert holder) component of the present disclosure.
Figure 5C:
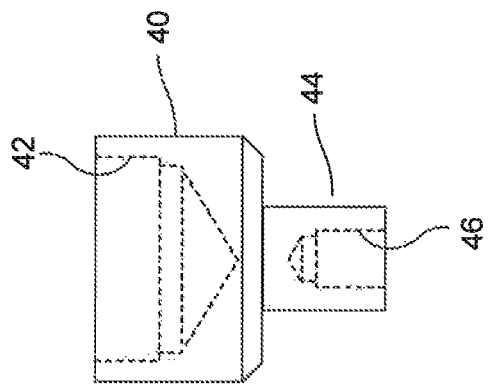
FIG. 5C is a cross-sectional view along plane 5C-5C of FIG. 5B.
Figure 5B:
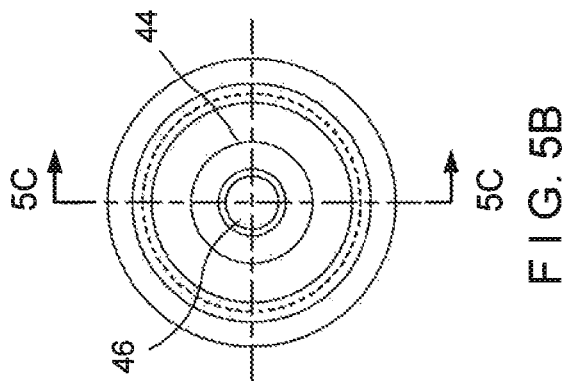
FIG. 5B is a top view, partially in perspective, of the top grip component of the present disclosure.
Figure 6A:
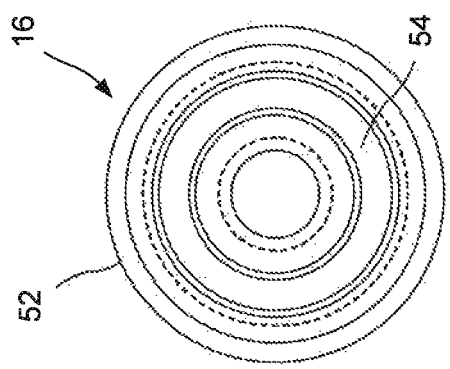
FIG. 6A is a perspective view, partially in phantom of the grip insert component of the present disclosure.
Figure 6B:
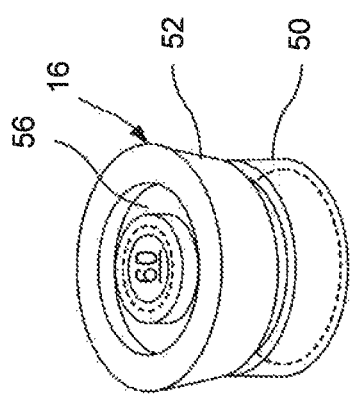
FIG. 6B is a top plan view, partially in phantom, of the grip insert component of the present disclosure.
Figure 6C:
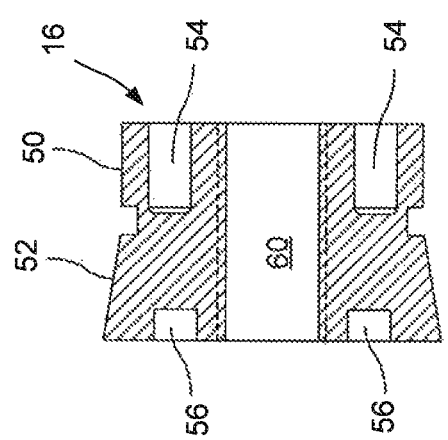
FIG. 6C is a cross-sectional view along plane 6C-6C of FIG. 6B.
Figure 6D:
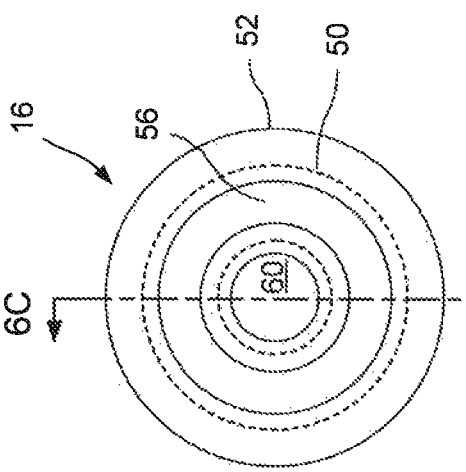
FIG. 6D is a bottom plan view, partially in phantom, of the grip insert component of the present disclosure.

As shown in FIGS. 5A, 5B and 5C, the top grip 12 (inverted with respect to FIG. 1) typically is rotationally symmetric and has two noted characteristics. The bottom portion of the top grip 12 is a cylindrical cup 40 with an internal wall 42 that is used to fasten it to the grip insert 16 (see FIGS. 6A, 6B, 6C and 6D). The top cylindrical portion 44 of the top grip 12 has a tapped aperture 46 on its top surface into which a screw (not shown) can be threaded so that it can be attached to another device (not shown) such as a pull-rod, shaft or load cell. One skilled in the art, after review of the present disclosure, would understand that routine equivalent substitutions could be made for the screws and similar elements. In some embodiments, the internal wall 42 may be threaded to allow for secure attachment to the grip insert 16. It is envisioned that alternative embodiments could combine the bottom grip 24 and a bottom grip holder into a single piece; combine the top grip 12 and the grip insert 16 into a single piece with a hollow core (wherein the resulting piece may removably engage a funnel); use a coating on the inner faces of the two-piece clamp 18 to eliminate the need for grip base rubber seals 30, 32; mold a seal into grip insert 16 and bottom grip 24 to eliminate the need for first and second O-rings 26, 28.

As shown in FIGS. 6A, 6B, 6C and 6D, grip insert 16 is typically rotationally symmetric and includes a generally cylindrical portion 50 for engagement with the top grip 12 and an outwardly flaring rotationally symmetric portion 52 for engagement with two-piece clamp 18. Cylindrical portion 50 includes a first circumferential groove 54 for seating cylindrical rubber seal 14. Moreover, in some embodiments, the outer cylindrical wall of cylindrical portion 50 may be threaded for engagement with internal wall 42 of top grip 12. Similarly, outwardly flaring rotationally symmetric portion 52 includes a second circumferential groove 56 for seating first O-ring 26. Grip insert 16 further includes a cylindrical bore 60 which may be threaded. The threads of cylindrical bore 60 typically increase the exposed surface area thereby increasing the gripping force on the material being molded into the top grip.

As shown in FIG. 1, the first O-ring 26 forms a seal between the grip insert 16 and the top of the two-piece clamp 18. Similarly, the second O-ring 28 forms a seal between the two-piece clamp 18 against the top face of the bottom grip 24.

As shown in FIGS. 9A, 9B and 9C, the bottom grip 26 is typically rotationally symmetric and has an upper cylindrical portion 62 and a lower cylindrical portion 66 of reduced diameter, along with a tapered portion 64 therebetween. A threaded blind axial bore 68 extends generally through the upper cylindrical portion 62 and the tapered portion 64. The internal threads within threaded blind axial bore 68 function similarly to the threads in the cylindrical bore 60 of the grip insert 16, increasing the exposed surface area thereby providing gripping force onto the material being molded within the grip 10.

Figure 7A:
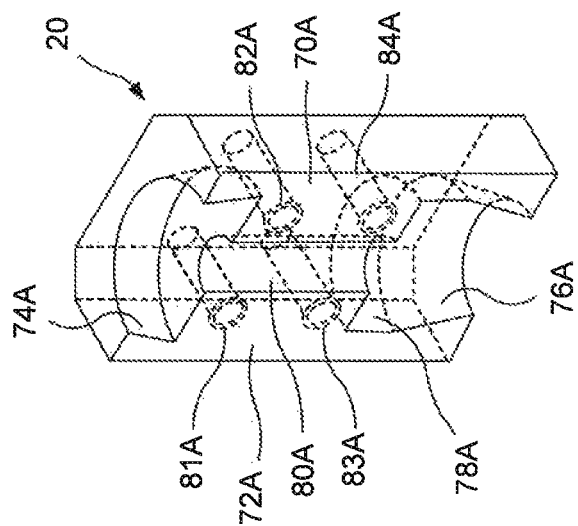
FIG. 7A is a perspective view, partially in phantom, of the threaded side of the body of the present disclosure.
Figure 7B:
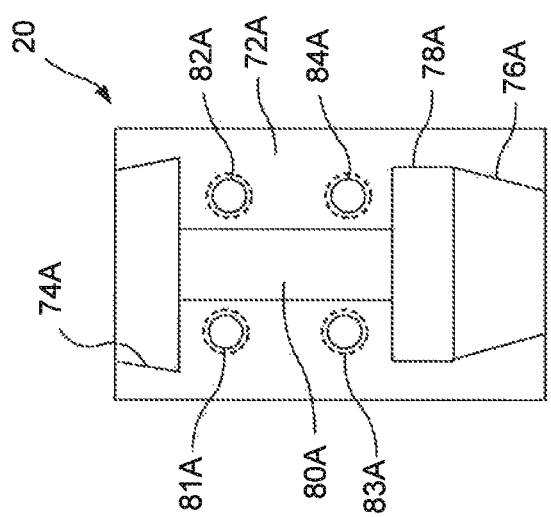
FIG. 7B is an interior plan view, partially in phantom, of the threaded side of the body of the present disclosure.

The elements 20, 22 of the two-piece clamp 18 are illustrated in FIGS. 7A, 7B, 8A, 8B, and 8C. Threaded side 20 is illustrated in FIGS. 7A and 7B. Threaded side 20 presents a relatively orthogonal outer face 70A while the inner planar face 72A includes an upper first undercut aperture portion 74A for engaging the outwardly flaring rotationally symmetric portion 52 of grip insert 16 and lower first undercut aperture portion 76A for engaging tapered portion 64 of bottom grip 26. Lower first undercut aperture portion 76A further includes first semi-cylindrical aperture portion 78A for engaging upper cylindrical portion 62 of bottom grip 26. A first semi-cylindrical axial bore portion 80A communicates between upper and lower first undercut aperture portions 74A, 76A. Four threaded apertures 81A, 82A, 83A, 84A pass transversely through the threaded side 20.

Counterbore side 22 is illustrated in FIGS. 8A, 8B and 8C. Counterbore side 20 presents a relatively orthogonal outer face 70B while the inner planar face 72B includes an upper second undercut aperture portion 74B for engaging the outwardly flaring rotationally symmetric portion 52 of grip insert 16 and lower second undercut aperture portion 76B for engaging tapered portion 64 of bottom grip 26. Lower second undercut aperture portion 76B further includes second semi-cylindrical aperture portion 78B for engaging upper cylindrical portion 62 of bottom grip 26. A second semi-cylindrical axial bore portion 80B communicates between upper and lower second undercut aperture portions 74B, 76B. Four countersunk apertures 81B, 82B, 83B, 84B pass transversely through the counterbore side 20.

Threaded side 20 and counterbore side 22 are aligned so that inner planar faces 72A, 72B are likewise aligned, with grip base rubber seals 30, 32 (which are shaped in accordance with inner planar faces 72A, 72B) therebetween, so that first and second undercut apertures portions 74A, 74B form an upper undercut aperture to engage the outwardly flaring rotationally symmetric portion 52 of grip insert 16. Likewise, lower first and second aperture portions 76A, 76B form an lower undercut aperture to engage the taper portion 64 of bottom grip 26, with first and second semi-cylindrical aperture portions 78A, 78B engaging upper cylindrical portion 62 of bottom grip and first and second semi-cylindrical axial bore portions 80A, 80B forming an axial bore thereby forming an axial bore which forms a substantial portion of the resulting mold. Threaded side 20 and counterbore side 22 are affixed to each other by passing screws 34 through countersunk apertures 81B, 82B, 83B and 84B and threadedly engaging threaded apertures 81A, 82A, 83A and 84A.

Several of the elements of the parts used in this disclosure were chosen for their practicality for a specific application in mind. Several elements could be eliminated, replaced or modified for other applications. For example:

1. the threads on the inside of cylindrical bore of grip insert 16 and threaded blind axial bore 68 of bottom grip 26 could be replaced with a knurled pattern, sawtooth pattern, smaller or larger thread, a wave pattern, or similar patterns or textures in order to increase the exposed surface area contacting the specimen or sample.

2. the threads used to mate the top grip 12 to the grip insert 16 could be replaced by another clamping method, such as a clevis, a magnet, a press fit, or similar configurations.

3. the first and second O-rings 26, 28 used to provide a seal between the grips 16, 26 and the two-piece clamp 18 could potentially be eliminated completely, replaced by a different type of seal or material.

4. the screws 34 used on the two-piece clamp 18 could be replaced by a different fastener, a clamp around two parts, or similar elements.

5. one skilled in the art, after review of the present disclosure, will understand that the materials, size of each one of the components, taper, chamfers, counter-bores, part shapes are all application dependent.

An application of this embodiment of the disclosure is to provide the user with a way to cast a fluid/gel/powder/compound/material into a mold, let it set/polymerize/solidify, remove the mold and end up with a solid sample that is clamped or held at both ends and pulled on so that its tensile strength or other mechanical properties can be measured. Performing tensile tests is a widely accepted, standard material testing method. A number of mechanical properties such as tensile strength, yield strength, modulus and creep can be measured by performing a tensile test on a sample.

A typical and intended protocol to use the embodiment of the disclosure starts off by having it assembled as a mold. This assembly is comprised of the bottom grip 26, a two-piece clamp 18 held together by four screws 34, a grip insert 16 and first and second O-rings 26, 28. The O-rings 26, 28 provide a face seal between the grip insert 16 and the two-piece clamp 18 and bottom grip 26 and two-piece clamp 18. Once these parts are assembled, a mold is formed wherein the middle of the grip insert 16, the bottom grip 26 and the two-piece clamp 18 have a middle cavity formed from the respective longitudinal bores. The center cavity space can be of any dimension or shape, depending on the material being tested, desired sample shape, test standard requirements, etc. First circumferential groove 54 on grip insert 16 allows the user to press fit a funnel 36 (see FIGS. 3, 4A, 4B and 4C) into the top of the grip insert 16.

Figure 3:
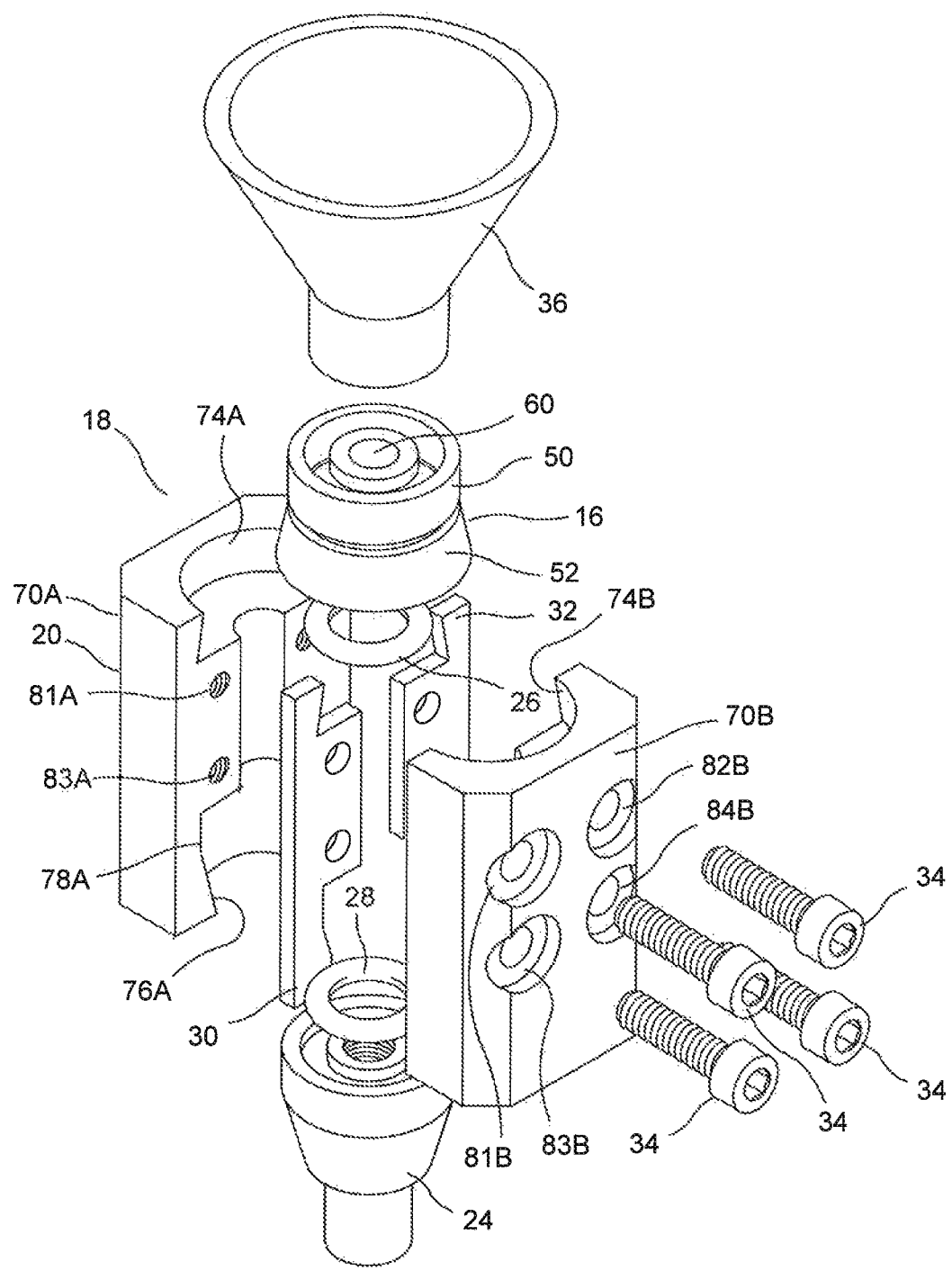
FIG. 3 is an exploded view of the grip of the present disclosure, shown with a funnel in place of a top grip.

As shown in FIG. 3, funnel 36 can be used to guide the fluid/gel/material into the mold of grip 10. In the specific case of the application this disclosure was designed for, a gel is dropped into the funnel and the entire assembly is centrifuged at high speeds, which forces the gel down into the mold of grip 10. The employed method for introducing the material to be tested into the mold of grip 10 is entirely application/protocol/test standard specific.

Once the fluid/gel material is in the mold of grip 10, the funnel 36 is removed and the fluid/gel/compound/material is given time to polymerize or solidify, if necessary. The top grip 12 can then be screwed or otherwise attached onto the grip insert 16.

Once this has occurred, the entire assembly is moved into a chamber body, such as, but not limited to, a bioreactor chamber body. The chamber body is not part of the disclosure and is not necessary for the embodiment of the disclosure to function. The chamber merely provides a structure or frame to install the mold cavity in. Another clamp mechanism is installed in the bottom of the chamber. The bottom grip 24 slips into the bottom clamp where it can be secured by tightening two screws. This locks the bottom grip into the chamber.

At this point, the user can attach a pull-rod or push-rod to the top grip 12 to support the weight of the grip 10 and the material. In a material test frame, the top grip 12 could be attached to a pull-rod or load cell. The two-piece clamp 18 can be removed from the assembly by removing the four screws 34. This leaves the top and bottom grips 12, 26 in the chamber and the cast gel/fluid in between the top and bottom grips 12, 26. The top grip 12 is secured in the chamber/frame by the pull-rod and the bottom grip 26 is secured in the chamber/frame by the bottom clamp.

With the top and bottom grips 12, 26 secured in a chamber or test frame, the user can perform a tensile or compression test on the material. It is noted that, unless otherwise indicated, all references to tensile testing refer likewise to compression testing.

The inside of the top and bottom grips 12, 26 are threaded (could be a groove, convolutions, a different thread or similar structures) to act as the gripping surface into the material. This gripping force is needed to ensure the material can be pulled on from both ends. The thread type, pitch and depth can all be changed depending on the material being tested and the specific application. Some stiff materials will not require deep threads where as soft materials will require deep threads to ensure proper retention of the material in the grips.

The resulting embodiment of grip 10 makes it possible to test very soft materials that could not be compressed or clamped into other existing grips. These grips typically have grip faces that come together to squeeze the sample 100 (see FIG. 10) and provide clamping force. The embodiment of the disclosure alleviates the need to clamp the material as the internal elements of the grips (such as, but not limited to, threads) to provide the clamping force of the grips. The material may become wedged into the threads. Very soft materials such as gels cannot be clamped in between grip faces. Doing this usually results in crushing the sample 100 or damaging its structure.

This embodiment of grip 10 reduces the number of operations required to get a sample 100 (see FIG. 10) in between top and bottom grips 12, 26. With this design, the material actually solidifies inside the grips 12, 26, which reduces the manipulation of the raw materials. A typical tensile test experiment setup would have the operator raise the crosshead on a load frame, open the grip faces, insert the sample in the grips, close the grips, adjust the height of the cross head and then run the test. Since the height of the embodiment is typically constant, the frame can always be set at the same height. The operator needs to insert the mold, clamp the bottom grip, clamp the top grip and remove the two-piece clamp. This could be done in less operations if the top and bottom clamps were hinged, leaving just one screw to tighten and if the number of screws to open the two-piece clamp 18 was reduced. The screws 34 used in the embodiment could easily be reduced and simplified for a quicker operation of the device.

This embodiment of grip 10 eliminates or reduces the possible contamination of the specimen by the user. This could be an important consideration when handling high purity materials with properties that can be affected by any form of contact.

This embodiment of grip 10 reduces significantly the risk of damaging a sample 100 during its installation in the grips or load frame 200 (see FIG. 10). Since the material is always handled and encased in a mold, the specimen is never handled directly. There are no adjustments to the sample position to make to align it in the grips or in the load frame, only the mold is positioned and coupled to the frame and the pull-rod/load cell or actuator before the test can begin.

This embodiment of grip 10 enables the quick production of test-ready samples. The tested material does not need to be transformed or manipulated to get it into a tensile test-ready shape. It forms directly into the grips the moment it enters the mold. Also, the mold (such as defined by first and second semi-cylindrical axial bore portions 80A, 80B) can be made into any shape or form, allowing for the testing of oddly shaped parts that would normally need to be machined, thus reducing the stresses put on the bare material. It also eliminates the need to transform or shape the material into a specific shape as defined by a specific test standard for that sort of material, device or part.

This embodiment of grip 10 provides the user with the ability to condition the sample prior to the test without coming into direct contact with the sample. For example, the two-piece clamp 18 could be outfitted with a heating pad or channels through which cooling or heating fluid is pumped or circulated to modulate the sample's temperature. This could benefit the user by reducing the sample's cool down time, accelerating its solidification or polymerization, bringing it to room temperature for further handling, bringing it to a standard's prescribed test temperature.

It should be noted that some embodiments may not include an entire inner bore which is hollow. In some applications, it may be useful to cast parts or samples that themselves have a hollow core, which would require an insert to be used in the center of the disclosed grip assembly.

Thus the several aforementioned objects and advantages are most effectively attained. Although preferred embodiments of the invention have been disclosed and described in detail herein, it should be understood that this invention is in no sense limited thereby.

What is claimed is:

1. A grip for materials testing, including:
    a clamp formed of a first clamp piece and a second clamp piece;
    the first clamp piece and the second clamp piece forming an interior mold chamber therebetween;
    the first clamp piece and the second clamp piece forming an upper engagement structure and a lower engagement structure;
    an upper grip element engaged by the upper engagement structure, the upper grip element including an upper interior volume which is in communication with the interior mold chamber; and
    a lower grip element engaged by the lower engagement structure;
    wherein the upper interior volume includes a first texture or pattern to increase exposed surface area therewithin; and
    the lower grip element includes a lower outwardly flaring wall, the lower engagement structure includes a lower undercut aperture, and the lower outwardly flaring wall is engaged by the lower undercut aperture.

2. The grip of claim 1 wherein the upper interior volume includes a second texture or pattern to increase exposed surface area therewithin.

3. The grip of claim 1 wherein the first texture or pattern is a threaded pattern.

4. The grip of claim 2 wherein the second texture or pattern is a threaded pattern.

5. The grip of claim 1 wherein a first portion of the lower undercut aperture is formed on the first clamp piece and second portion of the lower undercut aperture is formed on the second clamp piece.

6. The grip of claim 5 wherein the lower undercut aperture is formed and the lower outwardly flaring wall of the lower grip element is engaged by bringing the first and second clamp pieces together and aligning the first and second portions of the lower undercut aperture.

7. The grip of claim 1 wherein the upper engagement structure includes an insert element which engages the upper grip element and the first and second clamp pieces.

8. The grip of claim 7 wherein the insert element engages the upper grip element through an threaded engagement.

9. The grip of claim 7 wherein the insert element includes a circumferential groove for seating a seal or seating a funnel.

10. The grip of claim 8 wherein the insert element further includes an upper outwardly flaring wall, the upper engagement structure includes an upper undercut aperture, and the upper outwardly flaring wall is engaged by the upper undercut aperture.

11. The grip of claim 10 wherein a first portion of the upper undercut aperture is formed on the first clamp piece and second portion of the upper undercut aperture is formed on the second clamp piece.

12. The grip of claim 11 wherein the upper undercut aperture is formed and the upper outwardly flaring wall of the upper grip element is engaged by bringing the first and second clamp pieces together and aligning the first and second portions of the upper undercut aperture.

13. The grip of claim 12 wherein the upper grip element includes an upper external attaching element.

14. The grip of claim 13 wherein the lower grip element includes a lower external attaching element.

15. The grip of claim 1 wherein the first clamp piece and the second clamp piece can be separated from each other.

16. The grip of claim 1 wherein the first clamp piece and the second clamp piece are fastened to each other by a plurality of screws.

17. The grip of claim 1 further including grip seals between the first and second clamp pieces.

18. The grip of claim 1 wherein the upper and lower grip elements are rotationally symmetric.

* * * * *